United States Patent [19]
Gabriel

[11] Patent Number: 5,431,640
[45] Date of Patent: Jul. 11, 1995

[54] METHOD AND APPARATUS FOR DUODENAL INTUBATION OF A PATIENT

[75] Inventor: Sabry Gabriel, Macon, Ga.

[73] Assignee: The Medical Center of Central Georgia, Macon, Ga.

[21] Appl. No.: 336,492

[22] Filed: Nov. 9, 1994

[51] Int. Cl.$^6$ .......................................... A61M 31/00
[52] U.S. Cl. ...................................... 604/270; 600/9; 600/12
[58] Field of Search ............... 604/270, 49, 53, 54, 604/280, 282; 600/9, 12, 13

[56] References Cited

U.S. PATENT DOCUMENTS

| | | |
|---|---|---|
| 3,043,309 | 7/1962 | McCarthy . |
| 3,358,676 | 12/1967 | Frei . |
| 3,674,014 | 7/1972 | Tillander . |
| 3,794,041 | 2/1974 | Frei . |
| 3,847,157 | 11/1974 | Caillouette et al. . |
| 3,961,632 | 6/1976 | Moossun . |
| 4,077,412 | 3/1978 | Moossun . |
| 4,364,377 | 12/1982 | Smith ........................ 600/12 |
| 4,809,713 | 3/1989 | Grayzel . |
| 5,085,216 | 2/1992 | Henley, Jr. et al. ........... 604/270 X |
| 5,176,618 | 1/1993 | Freedman .................... 600/12 |
| 5,242,429 | 9/1993 | Nwaneri et al. ............... 604/270 |

Primary Examiner—John D. Yasko
Attorney, Agent, or Firm—Clifford A. Poff

[57] ABSTRACT

A method and apparatus for duodenal intubation of a patient is provided by establishing a force couple between a permanent magnet in the catheter tip and a hand held permanent magnet. The force couple is sufficiently great to impart a traction force to the catheter tip for advancing movement in the direction of bolus in the stomach beyond the pyloric sphincter and into the duodenum. Both magnets have an intense field of magnetic flux as formed by neodymium, iron, boron and dysprosium. The hand held magnet is of a size that can be grasped between the outstretched figures of a person performing the intubation procedure.

16 Claims, 6 Drawing Sheets

METHOD AND APPARATUS FOR DUODENAL INTUBATION OF A PATIENT

BACKGROUND OF THE INVENTION

1. Field of the Invention

The present invention relates to method and apparatus for duodenal intubation of a patient for administering nutrition into the small intestine, and, more particularly, to the selection and usage of permanent magnets to establish a traction force useful to advance the leading end of a catheter feeding tube along the stomach and through the pylorus and distal duodenum of the small intestine.

2. Description of the Prior Art

In the course of human illness there are many situations were the patient can not or will not eat food in the traditional manner to obtain needed nutrition which the patient must have or the healing process will not occur. Nutrients can be supplied to the patient through the use of a catheter. Modern science has developed numerous nutrients suitable for administering intravenously to a patient either peripherally in the arm or in some instances more centrally into a large vein in the neck. These nutrients can provide a high level of substance, even life saving for the patient whose intestinal tract is dysfunctional. However, problems can develop with intravenous introduction of the nutrition. The piercing of the skin to provide access for the small catheter to the vein, whether peripheral or central, also forms a route for infection to enter the body. Complications such as bleeding may occur and in instances where the catheter is placed centrally, the possibility exists to puncture the lung during the procedure of placing the catheter. The nutrients suitable for intravenous introduction have an extremely high cost which coupled with the potential for infection and other complications make it more desirable to supply the needed nutrition to the intestinal tract.

Figures 1, 2, 3:
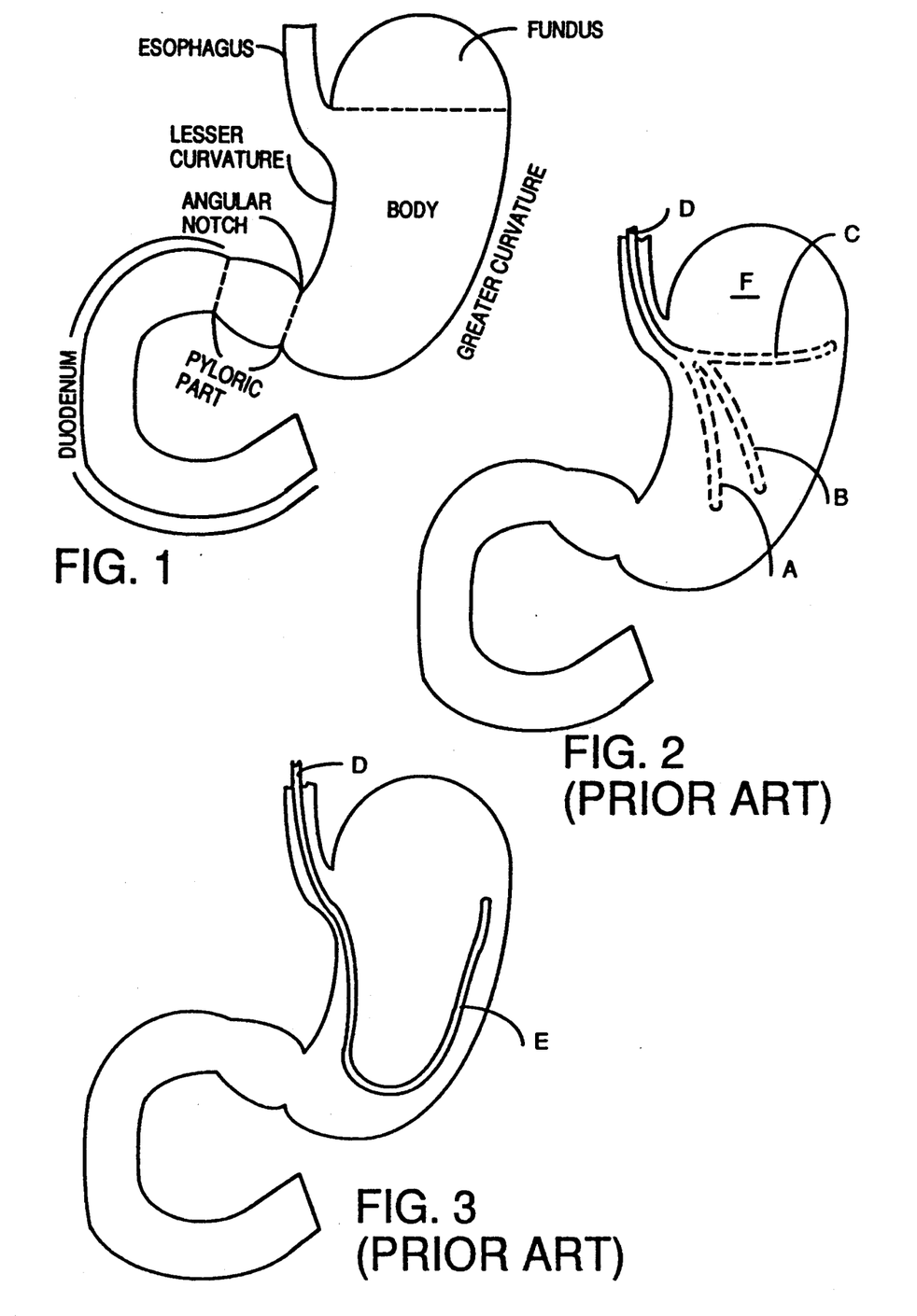
FIG. 1 is a schematic illustration of anatomical configuration of the stomach and duodenum together common nomenclature identifying salient parts for reference purposes.
FIG. 2 is a schematic illustration of three alternative tracts by the tip portion of the catheter entering the body of the stomach according to conventional prior art practices.
FIG. 3 is a schematic illustration of a typical undesired coil like tract of a catheter in the stomach commonly occurring according to a conventional prior art practice.

A known method for introducing nutrition to the intestinal tract is to supply the nutrition via a small tube introduced through a naris of the nose along the oesophagus through the stomach and beyond the pylorus into the duodenum of the small intestines. In FIG. 1 there is a pictorial illustration of anatomical configuration of the stomach and duodenum together common nomenclature identifying salient parts for reference purposes. The introduction of nutrients from the catheter to the duodenum adds to the patients immunity while the nutrients facilitate healing. Moreover, feeding a patient through the gut also prevents intestinal villi atrophy. Maintaining the intestinal villi intact prevents the translocation of bacteria from inside the gut of the patient to his blood stream.

When a catheter tube is advanced through the nose into the oesophagus and comes into the stomach, the tip of the catheter is no longer constrained to a course of travel as it was during movement along the nose and oesophagus. In contrast, the stomach cavity is large in a direction transverse to the direction of passage of bolus therein. Shown in FIG. 2 are three possible positions A, B and C for the leading part of a catheter D to assume upon entrance in the cavity of the stomach E. The cavity of the stomach merely contains the catheter tip as it is advanced but fails to constrain and guide for an intended course of travel to the pylorus. The flexible elasticity of the catheter usually allows a coiled configuration to be formed as shown in FIG. 3 as the catheter is advanced further into the stomach. The leading part of the catheter D is most likely to follow a return course of travel generally toward the oesophagus but following a path along the internal wall of the greater curvature of the body of the stomach. Continued introduction of the catheter moves the tip portion into the fundus where it executes a return course to the body of the stomach. It has been found that only about 10% of the attempted catheter placements using conventional placement techniques successfully negotiate the necessary course of travel in the stomach to the pylorus and thence to the duodenum. The incidence of successful placement of the catheter was usually a matter of random luck.

A common site to locate a misplaced catheter inside the stomach is at the fundus of the stomach. The anatomical configuration of the stomach can range from what is described as a hypotonic stomach to an atonic stomach. The variety to the size and configuration serves only to complicate the intubation of the patient. The tract of the catheter through the stomach must be made to follow the general J-shaped curvature of the stomach which becomes an extremely difficult procedure when the sole means available to control the catheter is the manipulation of the catheter at the entrance site through the patient's nose. Even after the stomach is traversed by the catheter tip, the tip must be advanced beyond the pyloric sphincter and into the duodenum before the introduction of nutrition since if the pyloric sphincter is not traversed by the catheter, a patient when lying flat and perhaps unconscious, might aspirate fluids from the stomach through the oesophagus to the lungs, leading to serious complications.

The tip of the catheter can be advanced along the stomach by peristaltic movement. Such movement may require three to five days and sometimes medication is necessary to irritate the stomach to increase the peristaltic movement. Serial X-rays, sometimes at twelve hour intervals, are necessary to verify the peristaltic movement of the catheter from the stomach through the pylorus to the duodenum. Not only is the patient exposed to frequent radiation of the incidence of X-rays, but also the time delay and added costs for the care and transporting the critically ill patient to a fluoroscope department or bring X-ray equipment to the patient are all undesirable.

The use of magnet flux in the placement of catheters and for a variety of purposes at a desired location is known in the art which includes the disclosures by U.S. Pat. No. 3,043,309 to McCarthy; U.S. Pat. No. 3,358,676 to Frei, et al.; U.S. Pat. No. 3,674,014 to Tillander; U.S. Pat. No. 3,794,041 to Frei et al.; U.S. Pat. No. 3,847,157 to Caillouette, et al.; U.S. Pat. No. 3,961,632 to Moossun; U.S. Pat. No. 4,077,412 to Moossun; and U.S. Pat. No. 4,809,713 to Grayzel. The McCarty U.S. Pat. No. 3,043,309 issued Jul. 10, 1962 describes the use of a localized magnetic field generated by an electrical magnet to manipulate a suction tube with a magnetic member at its tip through an intestinal obstruction under fluoroscopic visualization of the magnetic member. The use of an electromagnet is seen as essential because of the needed on/off control to allow turning it off while fluoroscopy radiation is used. Otherwise, the magnetic field generated by the electromagnet will distort any picture on the fluoroscopy screen or X-ray plate. The electrical magnet with its small pole surface area of about 1¼ square inches supply only a very localized depth of penetrating flux, thereby necessitating the use of fluoroscopy to capture the targeted magnetic member of the tube, all represent complex disadvantages. Moreover, the use of very strong electrical current in the order of 40 amperes through the coils of the electrical magnet which is applied to the patient represent an unwarranted risk and hazard. The remaining patents show a variety of instructions for the inclusions of a magnet in a catheter. The Frei U.S. Pat. No. 3,794,041 shows beads of magnetic material inserted in a body part with the catheter for moving the body part using an external magnet. The Caillouette U.S. Pat. No. 3,847,157 shows the use of a magnetic indicator in a medico-surgical tube used to identify the location of the tube. The Tillander U.S. Pat. No. 3,674,014 shows a tip portion of a catheter made of tandemly arranged magnetic sections with ball shaped ends so that the sections can deflect with respect to each other for guidance of the catheter tip. The Moossun U.S. Pat. No. 4,077,412 shows a trans-abdominal stomach catheter of the Foley type used to direct the placement of the catheter by way of an external puncture from the outside of the abdomen through the stomach wall. The Frei et al, U.S. Pat. No. 3,358,676 shows the use of magnets and for remotely controlling propulsion of a magnet through a duct of a human being to perform a function upon activation such as to effect a release of drugs at a predetermined location. The Grayzel U.S. Pat. No. 4,908,713 shows the use of a catheter for use for electrically pacing or excitation of the heart.

The need therefore exists to provide a method and apparatus for duodenal intubation of a patient to provide nutrition to the digestive tract beyond the stomach which will overcome the shortcomings and disadvantages of known intubation procedures.

It is an object of the present invention to provide a method and apparatus for duodenal intubation of a patient for duodenal intubation of a patient using an external hand-held permanent magnet having a pole face approximating the anatomic width of the stomach of the patient which can be moved about the abdomen of a patient to establish a flux coupling with a permanent magnet in the tip of a catheter of a magnitude sufficient to impart a traction force to the catheter for advancement along the stomach through the pylorus to the duodenum.

It is a further object of the present invention to provide a method and apparatus for duodenal intubation of a patient through the use of a permanent magnet having a physical size which can be grasped between the outstretched fingers of a person's hand and provide a magnetic pole face sufficiently large that flux lines will permeate the abdomen of the patient and form a flux coupling with a magnet in the tip of an intubation catheter and impart a traction force thereto while resident in the stomach of a patient.

SUMMARY OF THE INVENTION

More particularly, according to the present invention, there is provided a method for intubating a patient to introduce nutrition to the digestive tract beyond the stomach, the method including the steps of selecting an elongated flexible radio opaque catheter having a catheter permanent magnet in a distal end portion which is remote to an access channel communicating with a fluid conductive lumen of the catheter, introducing the distal end of the catheter through the stomach to the duodenum of the patient, arranging an external permanent magnet on the patient's abdomen to form a magnetic guidance path between the oesophagus and the pyloric part of a patient's stomach, the magnetic guidance path consisting of a field of magnetic flux enveloping the lesser curvature of the stomach, and imparting a traction force to the distal end portion of the catheter through a flux couple between the magnetic flux of the catheter permanent magnet and the magnetic flux enveloping the lesser curvature of the stomach to advance the catheter tip along the magnetic guidance tract.

The present invention further provides an apparatus to intubate the gastrointestinal track of a patient to introduce nutrition into the small intestine, the apparatus including the combination of an elongated flexible catheter having a permanent magnet at a distal end portion thereof, the catheter having an access channel extending to a lumen for conducting a nutrient to an eyelet communicating with the lumen at the distal end of the catheter upstream of the magnet, and an external permanent magnet having magnetic pole faces on a body of magnetic material defining a flux density of such character for forming a magnetic guidance path by permeating body tissue of the abdomen and defining by the field of magnetic flux enveloping the lesser curvature of the stomach, the field of magnetic flux being sufficiently dense to impart a traction force to the distal end portion of the catheter through a flux couple between the magnetic flux of the catheter permanent magnet and the magnetic flux of the external permeate magnet.

BRIEF DESCRIPTION OF THE DRAWINGS

The present invention will be more fully understood when the following description is read in light of the accompanying drawings in which.

DETAILED DESCRIPTION OF THE PREFERRED EMBODIMENTS

Figure 4:
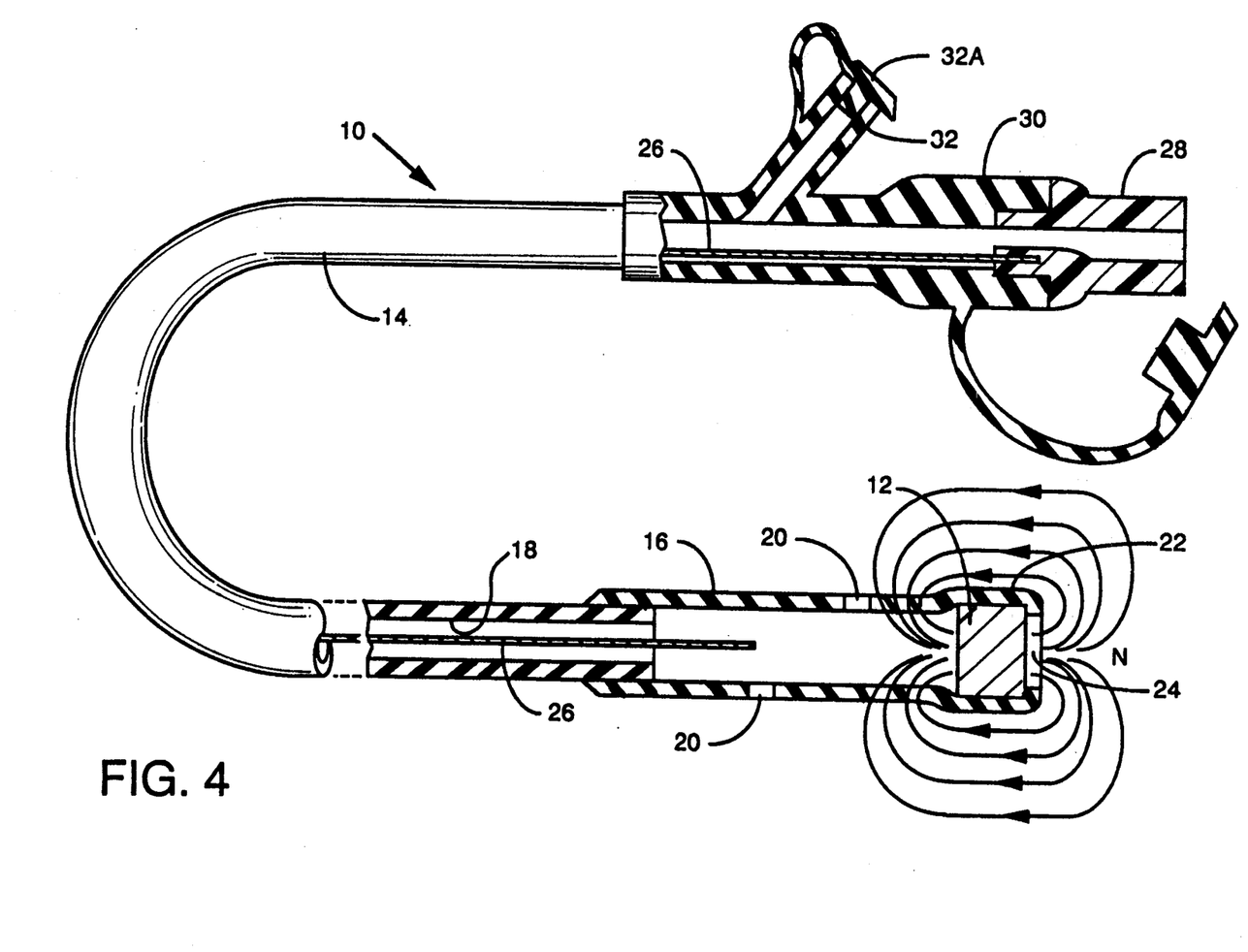
FIG. 4 is a plan view partly in section of a catheter embodying magnetic means in the distal tip thereof to facilitate the placement of the catheter according to the present invention.

In FIG. 4 there is illustrated a feeding tube catheter 10 embodying a modified construction according to the present invention by the inclusion of a cylinder shaped permanent magnet 12, preferably a magnet composition of neodymium, iron, boron and dysprosium as the supply source for magnetic flux. Such a magnet composition was chosen for the preferred embodiment because of the large field of magnetic flux enveloping the magnet between the magnetic poles.

As is well known, the catheter 10 is about 45 inches long and includes a radio opaque body portion 14 typically of a diameter of about 3 mm. At the distal end of the catheter there is a radio opaque tip portion 16 adhered to the end part of the body portion 14 and having an outside diameter typically of about 5 mm. A lumen 18 in the body portion 14 forms a fluid conducting relation with the internal cavity of the tip portion 16 which contains eyelet apertures 20 at spaced apart locations along the length of the tip portion for discharging and receiving fluids including supplying nutrients in fluid form to the small intestines of the patient after intubation. The magnet 12 has a diameter of about 5 mm. and a length of about 6 mm. which produces a slight bulge identified by reference numeral 22 when placed in the distal end of the tip portion 16. The magnet can be inserted into the tip portion through an opening 24 in the end wall of the tip portion. The magnetic polarity of the magnet is specifically chosen such that the north pole faces the opening in the tip of the tube which becomes a frame of reference for the orientation of a large hand-held magnet externally of the patient's body, as will be described in greater detail hereinafter. It is to be understood that the foregoing dimensional relation of the catheter tip portion and catheter magnet are only exemplary and catheters that are either larger or smaller as to their dimensional relation may be used to carry out the present invention.

Extending along the entire length of the lumen is a stylet 26 anchored in a cap 28. The stylet adds a desired degree of stiffness and rigidity to the catheter to facilitate the placement procedure. After placement of the catheter is completed, the cap is used for extracting the stylet from the catheter after which the lumen can be utilized for the supply of nutrients for the patient. The cap 28 is fitted to a cavity formed in a fixture 30 which is joined to the free end of the catheter opposite the tip portion 16 and provided with an additional duct section 32 having a removable closure cap 32A for access when it is desired to introduce and withdraw fluids from the lumen of the catheter. As will be explained in greater detail hereinafter, a syringe can be fitted to the duct section 32 in a fluid tight manner per se well known in the art.

Figure 5:
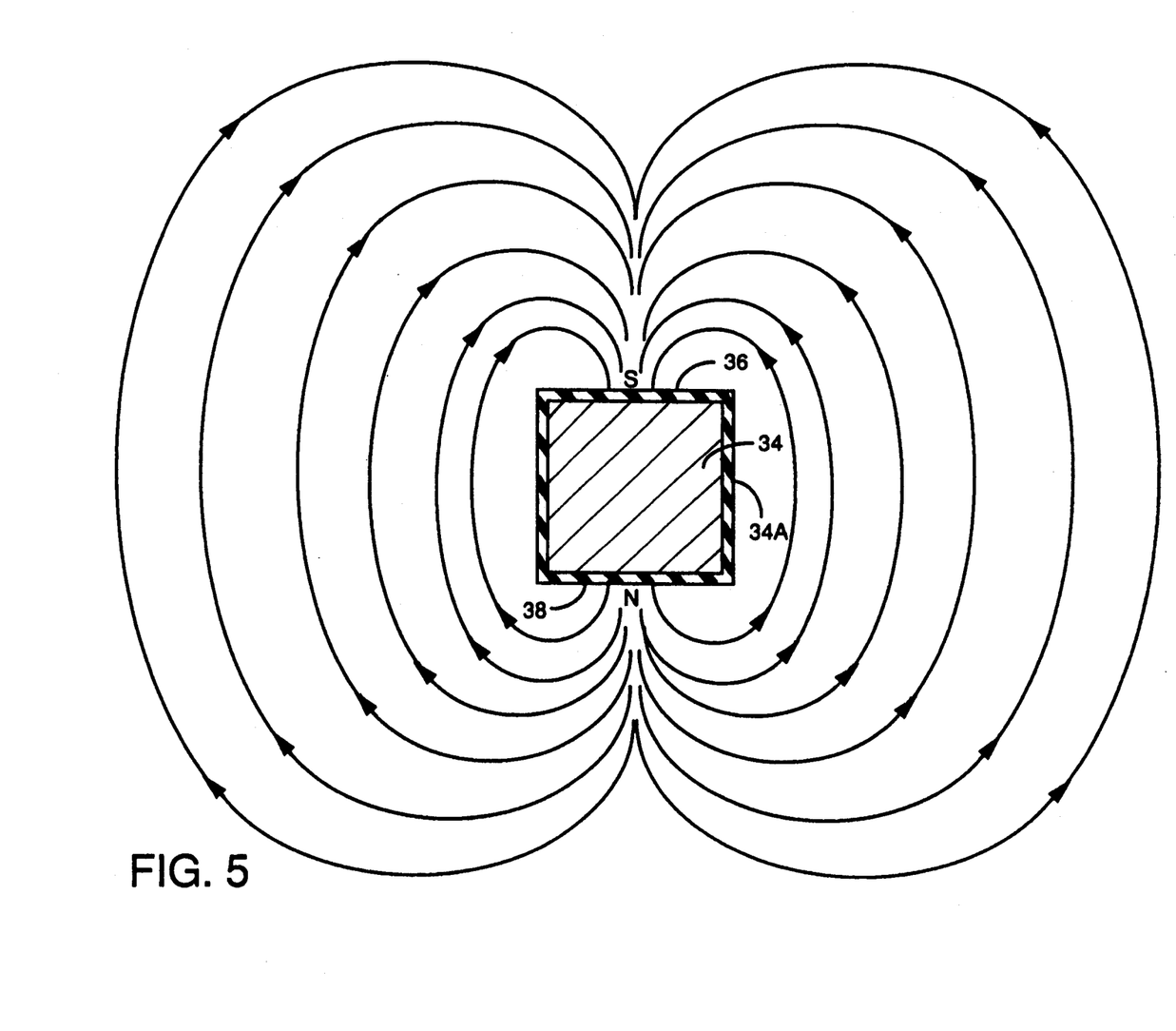
FIG. 5 is sectional view of a hand held permanent magnet used for applying a traction force to the catheter for placement in the duodenum.

In FIG. 5 there is illustrated a preferred form of a permanent magnet 34 which has a cylindrical sidewall between oppositely directed pole faces 36 and 38. Pole face 36 is selected to be the south pole and conveniently identified by the suitable label as "P" to signify the patient's side. The magnet 34 is made of a composition including neodymium, iron, boron and dysprosium and defines a physical size convenient to be grasped between the outstretched fingers of a person to support and move the magnet about a patient's body during the intubation procedure. The magnet 34, according to the present invention, is large as to its physical size, having a pole face with a diameter of at least about 3 inches, preferably about 3½ inches which forms a surface area in excess of 9 square inches whereby the pole face can be readily used to attain a stable attitude when brought into a contacting relation with a patient's body. The height of the magnet sidewall is at least about 4 inches, thus defining a volume to the permanent magnet flux field in the order of at least 36 cubic inches with at least 300 Gauss at 4 inches distance. The mass and composition of magnetic material forming the magnet are of such a character so as to thereby define a flux field that is extensive and far reaching beyond the area surrounding the volume of the magnet.

The magnet is protectively enveloped by a covering 34A of elastic material that will form a thermal barrier when contacting the patient's skin as well as protectively house the magnet against the fracture and possible loss of chips or pieces of the magnet in the event of accidental impact with a foreign object. The flux field in accordance with the present invention can permeate the body tissue to the thickness of the order of 6 inches or greater about an area sufficient to completely envelope the lesser curvature of the stomach. The density of the flux field is sufficiently great to interact as a force coupled with magnet 12 to establish and maintain a traction force to be imparted to the catheter tip through movement of the hand held permanent magnet.

Figure 6:
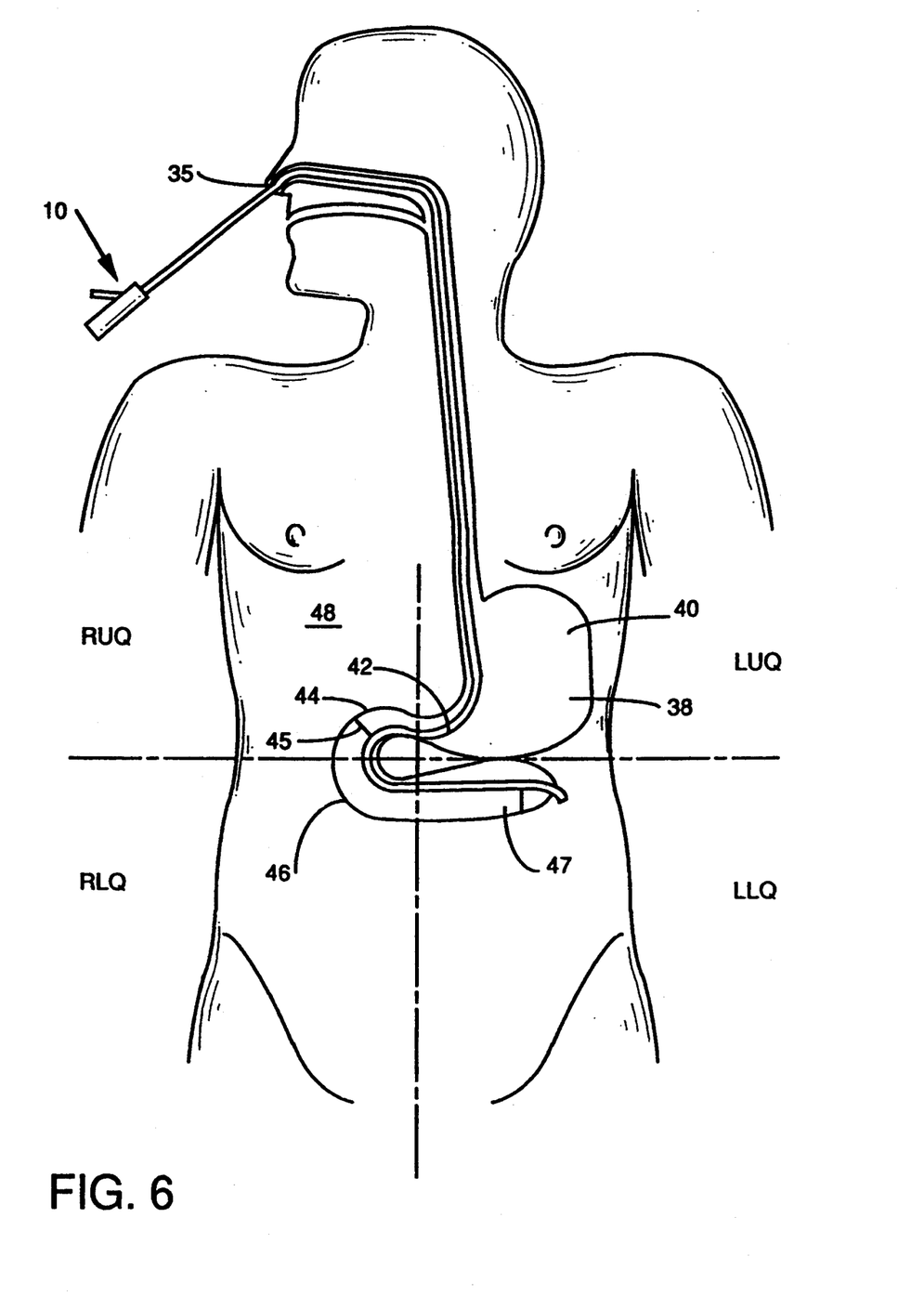
FIG. 6 is an illustration showing the path of the catheter within anatomical quadrants during passage through the stomach to the distal duodenum according to the present invention.

In FIG. 6 there is illustrated the portion of the human anatomy involved in the intubation process for providing nutrients to the small intestines, preferably the introduction of nutrients to the distal duodenum of the small intestines thereby preventing aspiration of fluids to the stomach. The tip portion 16 of the catheter 10 is preferably coated with a lubricant and numbing agent and then the tip portion is introduced into the naris 35 of the nose and advanced by the continued application of a compressive force to the catheter forcing the tip portion back to the backward portion of the patient's head and thence to the oesophagus. As is common, the passageway of the oesophagus affords ample guidance to the tip portion 16 whereupon it enters the body portion of the stomach 38 at the lower portion of the fundus. The movement of the catheter tip along the oesophagus and into the body of the stomach occurs within the left upper quadrant of the patient's body as indicated in FIG. 6.

Figures 7, 8:
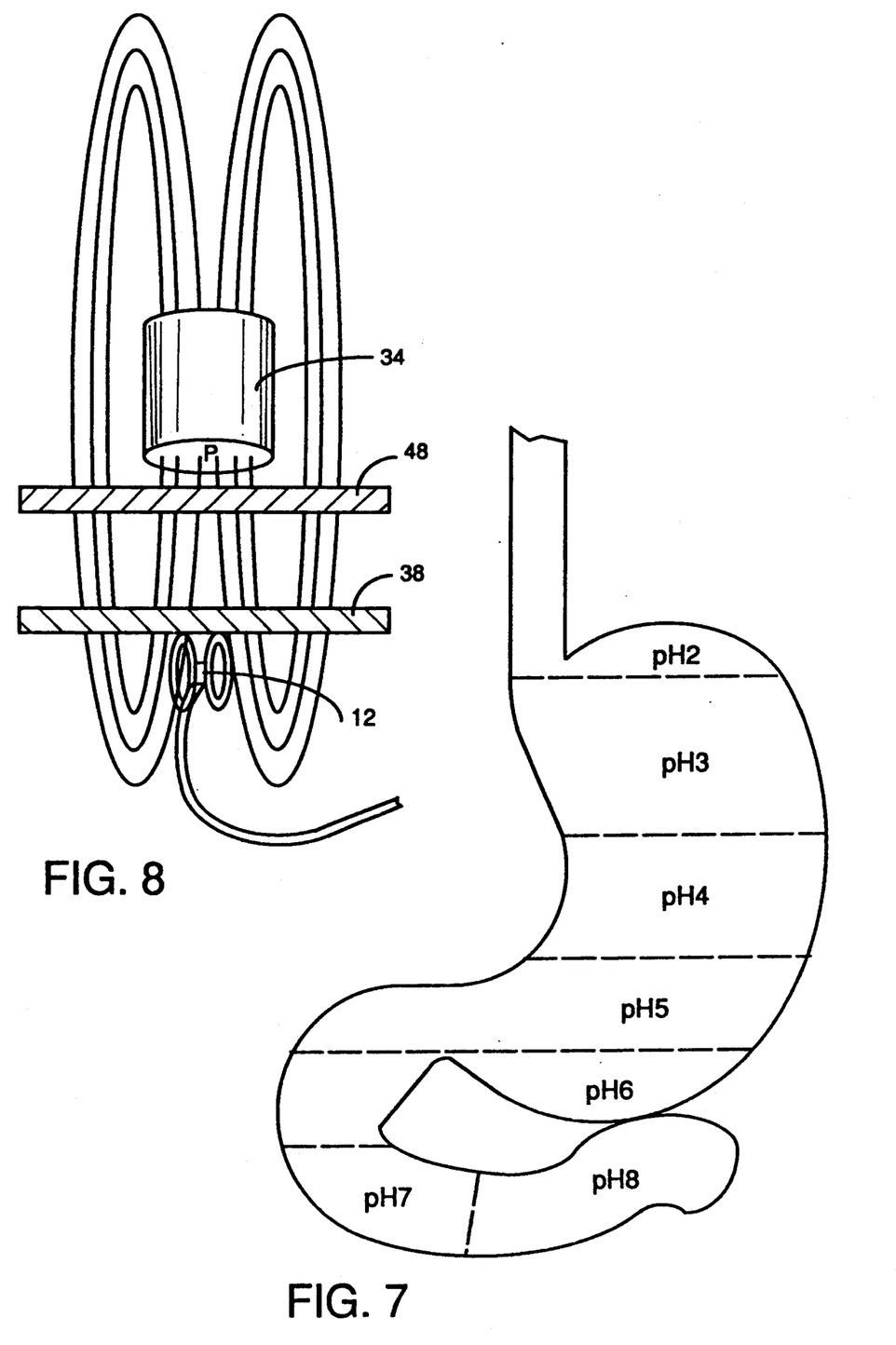
FIG. 7 is a schematic illustration identifying pH levels of various sites in the stomach and duodenum.
FIG. 8 is a schematic illustration of the flux coupling between the hand held a permanent magnet and the catheter permanent magnet through body tissue separating the abdominal and stomach walls during intubating a patient according to the present invention.

To establish the site of the tip portion in the stomach, a syringe is connected to duct section 28 the catheter 10 and operated to extract a specimen of fluid from the stomach. Litmus paper is then brought into contact with a specimen of the extracted fluid to establish a pH level which serves to identify a region in the stomach where the catheter tip resides. It is within the scope of the present invention to incorporate an electrode for a pH meter in the catheter tip and connect it by suitable wiring embedded in the material of the catheter wall to a meter to thereby provide pH levels and eliminate the need for extracting fluid samples during the procedure. In FIG. 7 there are demarkation lines separating regions wherein the pH level is given. In the area of the fundus a highly acidic condition exists in which the pH level of 3 will be detected and will turn the litmus paper to red. The pH level undergoes general regional changes as indicated in FIG. 7 whereby a neutral pH level will generally be found at the pyloric sphincter. In the duodenum, an alkaline condition exists as will be detected by an increasing pH level with a strong alkalinity condition being found in the distal duodenum of the small intestines from where a specimen sample will turn litmus paper dark green.

As can be seen from FIG. 6, the stomach has a generally J-shaped configuration extending with generally its largest transverse anatomical size at about the cardiac orifice, the entrance site to the stomach and then proceeding in the direction at which the stomach functions to advance bolus, the transverse dimension of the stomach narrows, and at an angular notch 42 which is generally at the border between the left upper quadrant, LUQ, and the right upper quadrant, RUQ. From the annular notch 42 there commences a smaller transverse dimension at the pyloric part 44 typically residing in the right upper quadrant together with pyloric sphincter 45. The pyloric sphincter, as is well known, is a muscular controlled closure which will dilate as when a bolus comes into contact with the sphincter. Beyond the sphincter, a bolus passes into the duodenum portion 46 that extends to the right lower quadrant, RLQ, and thence in a general horizontal direction into the left lower quadrant, LLQ, where the distal duodenum 47 of the small intestine is situated.

As is well known the generally J-shaped configuration of the stomach is arranged with the longer limb of the "J" lying to the left of the median plane and for the most part in the left upper quadrant. The long axis of the stomach passes downwards, forwards and then to the right and finally backwards and slightly upwards. The shape and size of the stomach varies greatly as in short, obese persons the stomach is high and transverse whereas in tall persons the stomach is elongated. It is also known that in a given patient the shape of the stomach depends on whether the stomach is full or empty, the position of the body, and the phase of respiration. At the cardiac orifice which is where the oesophagus enters the stomach an acute angle is formed by the passage way tending to always misdirect the tip of the catheter to the fundus rather than the body of the stomach.

Figure 9A:
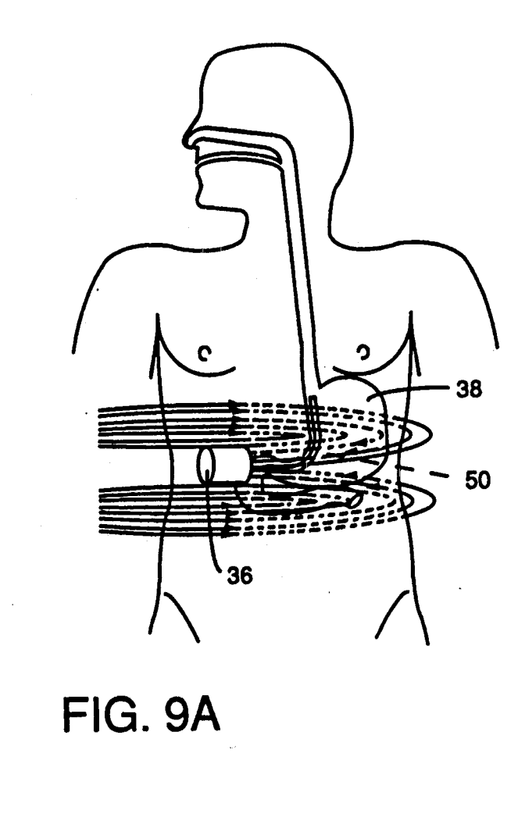
FIGS. 9A–9C are illustrations of the sequence of advancement by a catheter tip through the stomach beyond the pylorus to the distal duodenum by the positioning of the hand-held magnet relative to permanent catheter magnet to establish a traction force upon the catheter tip.

According to the present invention, a magnetic flux couple is established between the magnet 12 in the tip portion of the catheter in the stomach and magnet 34 when placed upon the abdomen of the patient. As shown in FIG. 9A, the pole face 36, designated as a south pole face, faces the patient and overlies the duodenum at the juncture with the pyloric part of the stomach. By arranging an external permanent magnet on the patient's abdomen in this manner there is formed a magnetic guidance path between the oesophagus and the pyloric part of a patient's stomach. The guidance path is shown by a line in FIG. 9A and identified by reference numeral 50 has a boundary formed by the lesser curvature of the stomach wall whereby the flux field permeating the guidance path acts through the magnetic couple to draw the catheter permanent magnet 12 toward the angular notch and into the pyloric part of the stomach. The traction force on the proximal pole of the magnet at the tip thus imparted to the catheter tip may be supplemented by a force imposed on the catheter tip due to continued advancing movement of the catheter into the patient's body at the naris. Thus, it can be seen that the field of magnetic flux is not only very dense but covers a broad area which is sufficient to envelope the lesser curvature area of the stomach. The flux field must have a magnetic polarity in a direction to impart a traction force to the distal end portion of the catheter by a magnetic flux couple and not a repulsive action which would serve to direct the catheter tip in the wrong direction away from the pyloric part of the stomach. During the course of travel by the catheter tip, through the use of the magnetic guidance path 50, samplings of fluid obtained from the stomach through the catheter by the use of a syringe can be periodically tested with litmus paper to confirm the progression of desired movement of the catheter tip through the stomach by the progressive change from high acidic toward neutral pH levels.

When it is confirmed by a fluid sample turning the litmus paper red that the site of the catheter tip portion 16 is in area 40 (FIG. 6) at the bottom of the fundus, the force couple relationship as best shown in FIG. 8 exist between the catheter tip portion 16 and the magnet 34. The magnetic force couple traverses a boundary wall of the stomach 38 and the body tissue separating the boundary wall from the surface of the abdomen 48. The force couple between the flux of magnet 34 and the flux of magnet 12 in their north-south pole relationship as discussed hereinbefore is sufficient that the surprising discovery was made that the position of the catheter tip could be controlled while advanced within the stomach in the direction of movement of a bolus. Magnet 34 imparts a traction force of a magnitude necessary to produce a corresponding advancing movement of the tip portion of the catheter. As explained previously, to facilitate such movement of the catheter, a slight compressive force may be applied to the catheter at the naris in a direction tending to advance the catheter to the stomach.

Figure 9B:
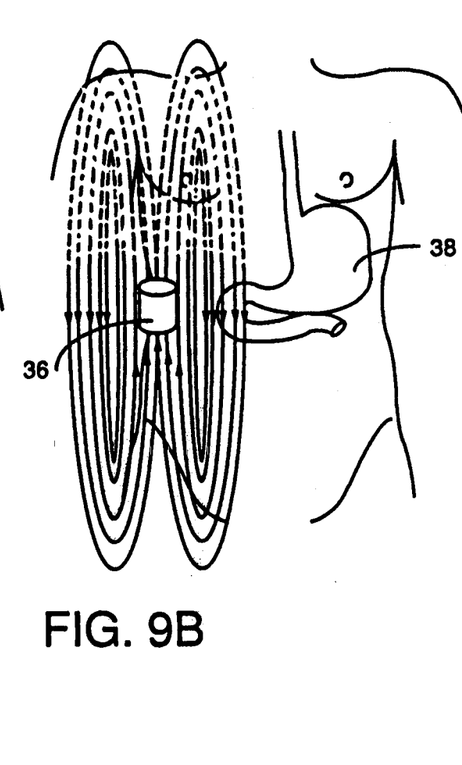
Figure 9C:
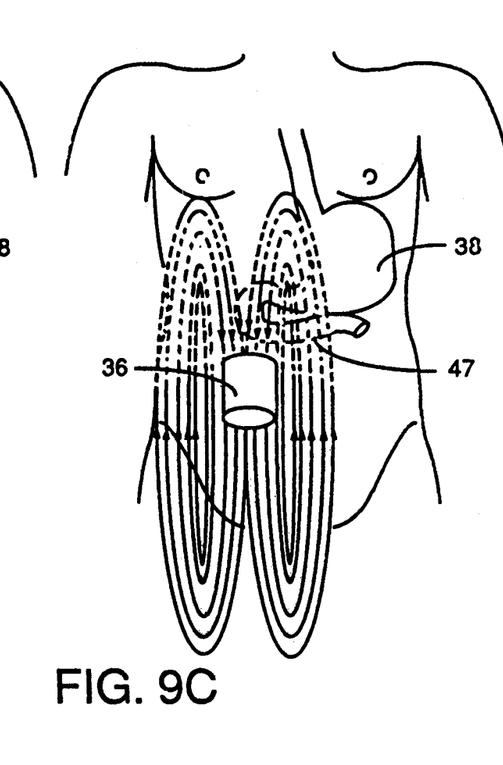

Returning to FIG. 9A, as the catheter tip is advanced along the pyloric part, the traction force is sufficient to draw the catheter tip against the wall of the pyloric sphincter thereby inducing dilation and penetration of the pyloric sphincter. As shown in FIG. 9B, when it is confirmed as by a litmus paper test of a pH level of about 7 or slightly alkaline, it will thereby indicate the catheter tip resides in the duodenum whereupon the magnet 34 is rotated 90° in a clockwise direction and shifted laterally away from the stomach to the side of the patient. The duodenum will be permeated by a dense field of strong magnetic flux and thereby impart a steering force combined with a traction force to the catheter tip, thus pulling the catheter tip downwardly through the second part of the duodenum to the terminus of the second part of the duodenum. A litmus paper test from fluid samplings will indicate a strong alkaline level whereupon the magnet 34 is rotated 180° to a position, as shown in FIG. 9C at the supra pubic area. The duodenum will be penetrated again by a dense field of strong magnetic flux which continues the established flux coupling resulting in the application of the traction force to the catheter tip advancing the catheter tip along the duodenum to the distal duodenum 47 of the small intestine.

When in the distal duodenum, a fluid sampling can be taken using the catheter which will turn litmus paper dark green thus indicating a strong alkaline condition. Before the introduction of nutrients to the distal duodenum of the small intestines using the catheter, final confirmation of the site of the catheter tip is to be made using X-Ray. Cap 28 is then used to extract the stylet from the lumen of the catheter which will then exhibit a marked increase to flexibility. Thereafter, as is well known in the art an infusion set can be connected to the duct in the fixture 30.

While the present invention has been described in connection with the preferred embodiments of the various figures, it is to be understood that other similar embodiments may be used or modifications and additions may be made to the described embodiment for performing the same function of the present invention without deviating therefrom. Therefore, the present invention should not be limited to any single embodiment, but rather construed in breadth and scope in accordance with the recitation of the appended claims.

I claim:

1. A method for intubating a patient to introduce nutrition to the digestive tract beyond the stomach, said method including the steps of:

selecting an elongated flexible catheter having a catheter permanent magnet in a distal end portion which is remote to an access channel communicating with a fluid conductive lumen of the catheter;

introducing the distal end of the catheter through the stomach to the duodenum of the patient;

arranging an external permanent magnet on the patient's abdomen to form a magnetic guidance path between the oesophagus and the pyloric part of a patient's stomach, said magnetic guidance path consisting of a field of magnetic flux enveloping the lesser curvature of the stomach; and imparting a traction force to the distal end portion of said catheter by a flux couple between the magnetic flux of said catheter permanent magnet and said magnetic flux enveloping the lesser curvature of the stomach to advance the catheter tip along said magnetic guidance tract.

2. The method according to claim 1 wherein said step of selecting an elongated flexible catheter includes selecting a catheter magnet having opposed pole faces arranged in planes transverse to the elongated length of the catheter.

3. The method according to claim 2 wherein said step of selecting an elongated catheter further includes orientating the catheter magnet such that the magnetic pole of the pole face facing in the direction of advancing movement of the catheter is attractive to the magnetic pole of the pole face of the selected permanent magnet facing the abdomen of the patient.

4. The method according to claim 1 wherein the catheter magnet and permanent magnet have a composition of neodymium, iron, boron and dysprosium.

5. The method according to claim 1 including the further step of confirming the placement site of the catheter tip beyond the pylorus in the small intestines by X-ray and thereafter introducing nutrients to the small intestines of the patient from the lumen of the catheter from a supply communicating with said access channel.

6. The method according to claim 1 including the further step of establishing the place of residence of the catheter tip during said step of imparting a traction force by the relative pH of the fluid at the tip of the catheter.

7. The method according to claim 6 wherein said step of establishing the place of residence includes using litmus paper for measuring the acidity and alkalinity of the fluid at the tip of the catheter.

8. The method according to claim 6 wherein said step of establishing the place of residence includes using a pH probe monitor incorporated in said catheter.

9. The method according to claim 7 including the further step of confirming the placement site of the catheter tip beyond the pyloric sphincter in the small intestines by X-ray and thereafter introducing nutrients to the small intestines of the patient from the lumen of the catheter from a supply communicating with said access channel.

10. The method according to claim 1 wherein said step of imparting a traction force to guide the distal end of the catheter includes angling of the pole face of the permanent magnet to said second position to envelope the duodenum with a field of magnetic flux and maintain a traction force on the proximal pole of the magnet at the tip of the catheter after traversing the anatomical length of the stomach.

11. The method according to claim 1 wherein said step of selecting an elongated catheter includes selecting a catheter having at least one eyelet communicating with said lumen and arranging said catheter magnet in said lumen at the distal end thereof to maintain fluid communication between the lumen.

12. The method according to claim 11 including the further step of using said eyelet to pass said catheter magnet to the distal end of the catheter.

13. The method according to claim 1 including the step of imparting compressive forces to the catheter in a direction of the extended length thereof at the entry site of the catheter in the body of the patient for said step of introducing the distal end of the catheter into the stomach of the patient.

14. An apparatus to intubate a patient to introduce nutrition into the small intestine, said apparatus including the combination of:

an elongated flexible catheter having a permanent magnet at a distal end portion thereof, said catheter having an access channel extending to a lumen for conducting a nutrient to an eyelet communicating with the lumen at the distal end of the catheter upstream of the magnet; and an external permanent magnet having magnetic pole faces on a body of magnetic material defining a flux density of such character for forming a magnetic guidance path by permeating body tissue of the abdomen and defining by the field of magnetic flux enveloping the lesser curvature of the stomach, the field of magnetic flux being sufficiently dense to impart a traction force to the distal end portion of the catheter through a flux couple between the magnetic flux of the catheter permanent magnet and the magnetic flux of said external permeate magnet.

15. The apparatus according to claim 14 wherein said magnetic pole faces are at opposite ends of a magnetic mass.

16. The apparatus according to claim 14 further including a protective enclosure about the periphery of said external permanent magnet.

* * * * *